US008940485B2

(12) United States Patent
Liang et al.

(10) Patent No.: US 8,940,485 B2
(45) Date of Patent: *Jan. 27, 2015

(54) METHODS FOR GENOTYPING MATURE COTTON FIBERS AND TEXTILES

(75) Inventors: Ming-Hwa Liang, Stony Brook, NY (US); Stephane Shu Kin So, Stony Brook, NY (US)

(73) Assignee: APDN (B.V.I.) Inc., Tortola, B.V.I. (VG)

( * ) Notice: Subject to any disclaimer, the term of this patent is extended or adjusted under 35 U.S.C. 154(b) by 0 days.

This patent is subject to a terminal disclaimer.

(21) Appl. No.: 12/269,757

(22) Filed: Nov. 12, 2008

(65) Prior Publication Data

US 2010/0279282 A1    Nov. 4, 2010

(51) Int. Cl.
C12Q 1/68 (2006.01)

(52) U.S. Cl.
CPC ........ C12Q 1/6895 (2013.01); C12Q 2600/156 (2013.01)
USPC ............................................................ 435/6.11

(58) Field of Classification Search
None
See application file for complete search history.

(56) References Cited

U.S. PATENT DOCUMENTS

| | | | |
|---|---|---|---|
| 4,183,989 A | 1/1980 | Tooth | |
| 4,739,044 A | 4/1988 | Stabinsky | |
| 4,757,141 A | 7/1988 | Fung et al. | |
| 5,047,519 A | 9/1991 | Hobbs, Jr. et al. | |
| 5,132,242 A | 7/1992 | Cheung | |
| 5,139,812 A | 8/1992 | Lebacq | |
| 5,151,507 A | 9/1992 | Hobbs, Jr. et al. | |
| 5,429,952 A | 7/1995 | Garner et al. | |
| 5,602,381 A | 2/1997 | Hoshino et al. | |
| 5,639,603 A | 6/1997 | Dower et al. | |
| 5,763,176 A | 6/1998 | Slater et al. | |
| 5,776,713 A | 7/1998 | Garner et al. | |
| 5,866,336 A | 2/1999 | Nazarenko et al. | |
| 5,942,444 A | 8/1999 | Rittenburg et al. | |
| 5,989,823 A | 11/1999 | Jayasena et al. | |
| 6,030,657 A | 2/2000 | Butland et al. | |
| 6,057,370 A | 5/2000 | Weiland et al. | |
| 6,127,120 A | 10/2000 | Graham et al. | |
| 6,140,075 A | 10/2000 | Russell et al. | |
| 6,169,174 B1 | 1/2001 | Hasegawa et al. | |
| 6,312,911 B1 | 11/2001 | Bancroft et al. | |
| 6,342,359 B1 | 1/2002 | Lee et al. | |
| 6,399,397 B1 | 6/2002 | Zarling et al. | |
| 6,576,422 B1 | 6/2003 | Weinstein et al. | |
| 6,686,149 B1 | 2/2004 | Sanchis et al. | |
| 6,743,640 B2 | 6/2004 | Whitten et al. | |
| 6,995,256 B1 | 2/2006 | Li et al. | |
| 7,060,874 B2 | 6/2006 | Wilkins | |
| 7,115,301 B2 | 10/2006 | Sheu et al. | |
| 7,160,996 B1 | 1/2007 | Cook | |
| 7,223,906 B2 | 5/2007 | Davis | |
| 2002/0048822 A1 | 4/2002 | Rittenburg et al. | |
| 2002/0187263 A1 | 12/2002 | Sheu et al. | |
| 2003/0142704 A1 | 7/2003 | Lawandy | |
| 2003/0142713 A1 | 7/2003 | Lawandy | |
| 2003/0162296 A1 | 8/2003 | Lawandy | |
| 2003/0177095 A1 | 9/2003 | Zorab et al. | |
| 2004/0063117 A1 | 4/2004 | Rancien et al. | |
| 2004/0166520 A1 | 8/2004 | Connolly | |
| 2004/0219287 A1 | 11/2004 | Regan et al. | |
| 2005/0059059 A1 | 3/2005 | Liang | |
| 2005/0214532 A1 | 9/2005 | Kosak et al. | |
| 2006/0017957 A1 | 1/2006 | Degott et al. | |
| 2006/0017959 A1 | 1/2006 | Downer et al. | |
| 2006/0117465 A1 | 6/2006 | Willows et al. | |
| 2006/0121181 A1 | 6/2006 | Sleat et al. | |
| 2006/0286569 A1 | 12/2006 | Bar-Or et al. | |
| 2007/0048761 A1 | 3/2007 | Reep et al. | |
| 2011/0289022 A1 | 11/2011 | Arioli | |

FOREIGN PATENT DOCUMENTS

| | | |
|---|---|---|
| GB | 2434570 | 8/2007 |
| RU | 2170084 C1 | 10/2001 |
| WO | WO 8706383 | 10/1987 |
| WO | WO 9014441 | 11/1990 |
| WO | WO 9606249 | 8/1994 |
| WO | 1403333 A1 | 1/1995 |
| WO | WO 9502702 A1 | 1/1995 |
| WO | WO 9745539 A1 | 12/1997 |
| WO | WO 9806084 | 2/1998 |
| WO | WO 9959011 | 11/1999 |
| WO | WO 0055609 | 9/2000 |
| WO | WO 0125002 A1 | 4/2001 |
| WO | WO 0199083 A1 | 12/2001 |
| WO | WO 02/057548 A1 | 7/2002 |

(Continued)

OTHER PUBLICATIONS

Altaf-Khan et al (Journal of Crop Improvement, vol. 16, pp. 1-20).*
Schuelke, Nature Biotechnology, 2000, 18, pp. 233-234.*
Cronn, American Journal of Botany, 2002, vol. 89, pp. 797-725.*
Hussein et al. Molecular Characterization of Cotton Genotypes Using PCR-based Markers. Journal of Applied Sciences Research 3(10): 1156-1169 (2007).
Jiang et al. Polyploid formation created unique avenues for response to selection in *Gossypium* (cotton). Proceedings of the National Academy of Sciences USA. vol. 95 pp. 4419-4424, Apr. 1998.

(Continued)

*Primary Examiner* — Michele K Joike

*Assistant Examiner* — Mindy G Brown

(74) *Attorney, Agent, or Firm* — F. Chau & Associates, LLC

(57) ABSTRACT

Methods for distinguishing between cotton cultivars of a specific species by analyzing a sample of mature cotton fibers from raw cotton materials or from textile goods are disclosed. DNA is extracted from the mature cotton fiber sample and subjected to PCR techniques which enable the identification of the cultivar of a particular cotton species utilized in the textile or cotton material of interest.

31 Claims, 2 Drawing Sheets

(56) References Cited

FOREIGN PATENT DOCUMENTS

| WO | WO 02084617 A1 | 10/2002 |
|---|---|---|
| WO | WO 03030129 A2 | 4/2003 |
| WO | WO 03080931 A1 | 10/2003 |
| WO | WO 2004025562 A1 | 3/2004 |

OTHER PUBLICATIONS

Lee et al. The complete chloroplast genome sequence of *Gossypium hirsutum*: organization and phylogenetic relationships to other angiosperms. BMC Genomics 7:61, Mar. 2006.

Ibrahim et al. Complete nucleotide Sequence of the Cotton (*Gossypium barbadense* L.) Chloroplast Genome with a Comparative Analysis of sequences among 9 Dicot Plants. Genes and Genetic Systems vol. 81, pp. 311-321.

Versalift, "Market Growth: the evolution of the serial life industry," Oct. 1, 2002. Accessed on web Nov. 10, 2008.

Schultz et al., "Archived or directly swabbed latent fingerprints as a DNA source for STR typing," Forensic Science International 127 (2002) 128-130.

Zuckermann et al. "Efficient methods for attachment of thiol specific probes to the 3' ends of synthetic oligodeoxyribonucleotides," Nucleic Acids Research, vol. 15, pp. 5305-5321 (1987), IRL Press Limited, Oxford England.

Whitcombe et al. "Detection of PCR products using self-probing amplicons and fluorascience." Nature Biotechnology, vol. 17, pp. 804-807 (1999) Nature America Inc. New York.

Tyagi et al. "Multicolor molecular beacons for allele discrimination," Nature Biotechnology, vol. 15, pp. 49-53 (1997) Nature Publishing Group, New York.

Nazarenko, et al. "A closed tube format for amplification and detection of DNA based on energy transfer," Nucleic Acids Research, vol. 25, pp. 2516-2521 (1997), Oxford Univeristy Press.

Tyagi & Kramer. "Molecular Beacons: Probes that Flouresce upon Hybridization," Nature Biotechnology, vol. 14, pp. 303-308 (1996) Nature Publishing Group, New York.

Sproat, et al. "The synthesis of protected 5'- mercapto-2', 5'-dideoxyribonucleoside-3-O-phosphoramides: uses of 5'-mercapto-oligodeoxyribonucleotides," Nucleic Acids Research vol. 15, pp. 4537-4848 (1987). IRL Press Limited, Oxford, England.

Nelson et al. "Bifunctional oligonucleotide probes synthesized using a novel CPG support are able to detect single basic pair mutations," Nucleic Acids Research, vol. 17, pp. 7187-7194 (1989). IRL Press Limited, Oxford, England.

Gupta et al "A general method for the synthesis of 3'-sulfnydryl and phosphate group containing oxgonucleotides," Nucleic Acids Research, vol. 19, pp. 3019-3025 (1991). Oxford University Press, Oxford, England.

Lee et al. "Allelic discrimination by nick-translation PCR with flourogenic probes," Nucleic Acids Research, vol. 21, pp. 3761-3766 (1993). Oxford University Press, Oxford, England.

Holland, et al. "Detection of specific polymerase chain reaction product product by utilizing the 5'[10]3'exonuclease activity of Thermus aquaticus DNA polymerase," Proceedings of the National Academy of Sciences, vol. 88, pp. 7276-7280 (1991) National Academy of Sciences, Washington D.C.

Heid, et al. "Real Time Quantitative PCR," Genome Research, vol. 5, pp. 986-994 (1996), Cold Spring Harbor Laboratory Press, Woodbury, New York.

Gibson, et al. "A Novel Method for Real Time Quantitative RT-PCR" Genome Research, vol. 6, pp. 995-1001 (1996) Cold Spring Harbor Laboratory Press, Woodbury, NY.

Agrawal & Tang, "Site-specific functionalization of olgodeoxynucleotide for non-radioactive labelling," Tetrahedron Letters, vol. 31, pp. 1543-1546 (1990), Pergamon Press, Great Briton.

Van De Ruke et al "Up-converting phosphor reporters for nucleic acid microarrays," Nature Biotechnology, vol. 19, pp. 273-276 (2001), Nature Publishing Group, New York.

Corstjens et al. "Infrared up-converting phosphors for bioassays," IEE Proceedings—Nanobiotechnology, vol. 152 pp. 64-72 (2005), Institution of Engineering and Technology. London.

Han, Z., et al., Characteristics, development and mapping of *Gossypium hirsutum* derived EST-SSRs in allotetraploid cotton. Theor. Appl. Genet. (2006) vol. 112, pp. 430-439.

Yang, L., et al., Validation of a cotton-specific gene, Sad1, used as an endogenous reference gene in quantitative and real-time quantitative PCR detection of transgenic cottons. Plant Cell Rep. (2005) vol. 24, pp. 237-245.

Dolnik, V., et al., Capillary Electrophoresis on microchip. Electrophoresis (2000) vol. 21, pp. 41-54.

Reinische, et al., "A Detailed RFLP Map of Cotton, *Gossypium hirsutum* x *Gossypium barbadense*: Chromosome Organization and Evolution in a Disomic Polyploid Genome." Genetics Society of America, pp. 829-847 1994.

Paterson, et al., "A Rapid Method for Extraction of Cotton (*Gossypium* spp.) Genomic DNA Suitable for RFLP or PCR Analysis." Plant Molecular Biology Reporter, vol. 11(2) 1993.

Chaudhary, et al., "Global Analysis of Gene Expression in Cotton Fibers from Wild and Domesticated *Gossypium barbadense*." Evolution & Development, vol. 10(5) pp. 567-582 (2008).

Hovav, et al., "A Majority of Cotton Genes are Expressed in Single-Celled Fiber." Planta, vol. 227 pp. 319-329 (2008).

Hussein, et al., "Molecular Characterization of Cotton Genotypes Using PCR-based Markers." Journal of Applied Sciences Research, vol. 3(10) pp. 1156-1169 (2007).

Ji, el al., "Isolation and Analyses of Genes Preferentially Expressed During Early Cotton Fiber Development by Subtractive PCR and cDNA Array." Nucleic Acids Research, vol. 31(10) pp. 2534-2543 (2003).

Jiang, et al., "Polyploid Formation Created Unique Avenues for Response to Selection in *Gossypium* (Cotton)." Proceedings of the National Academy of Sciences of the United States of America, vol. 95 pp. 4419-4424 (1998).

Lui, et al., "Chromosomal Assignment of Microsatellite Loci in Cotton." The Journal of Heredity, vol. 91(4) pp. 326-332 (2000).

Tu, et. al., "Suitable Internal Control Genes for qRT-PCR Normalization in Cotton Fiber Development and Somatic Embryogenesis." Chinese Science Bulletin, vol. 52(22) pp. 3110-3117 (2007).

Vos, et al., "AFLP: A New Technique for DNA Fingerprinting." Nucleic Acids Research, vol. 23(21) pp. 4407-4414 (1995).

Wendel Lab "DNA Extraction" Dec. 2001. Retrieved from web Aug. 15, 2011.

Federal Trade Commision, et al., "Calling It Cotton: Labeling & Advertising Cotton Products." Jul. 1999. Retrieved on web Sep. 1, 2001.

\* cited by examiner

US 8,940,485 B2

METHODS FOR GENOTYPING MATURE COTTON FIBERS AND TEXTILES

CROSS REFERENCE

This application is simultaneously co-filed with the patent application titled "Methods for Genetic Analysis of Textiles/Fabrics made of *Gossypium Barbadense* and *Gossypium Hirsutum* Cotton"; the co-filed patent application being hereby incorporated by reference.

FIELD

This invention pertains to methods for analyzing mature cotton fibers for the detection of genetic variations among a variety of cotton cultivars of a cotton species, particularly, cultivars of the cotton species *Gossypium barbadense* and *Gossypium hirsutum*.

BACKGROUND

In general, there are two major types of cotton species being cultivated throughout the world, namely *Gossypium barbadense* and *Gossypium hirsutum*. These two species are from the genus *Gossypium*, which comprises at least 40 different cotton species. *Gossypium barbadense* (sea island cotton) and *Gossypium hirsutum* (upland cotton) are allotetraploids and are known as New World cotton or "American" cotton. There are striking differences in the physical characteristics of the cotton fibers produced by *G. barbadense* compared to the cotton fibers produced by *G. hirsutum*. *G. barbadense* produces longer cotton fibers than most other cotton species and these fibers are usually called "extra long staple" (ELS) fibers, while those of *G. hirsutum* are shorter and are called or defined as "upland" fibers. Textiles made of ELS fibers are considered to be of higher quality compared to textiles made with shorter fibers, like those produced by *G. hirsutum* cotton plants. Thus, textiles produced from ELS cotton fibers are considered more valuable in the textile marketplace.

Many regions around the world produce ELS cottons with distinct fiber qualities, such as Egyptian Pima and Indian Pima. Despite the common ancestry, over time, isolation and/or cross breeding of a cotton species has created subtle but unique genetic variations in cultivars from different regions. Even though these cotton types belong to the same species, *G. barbadense*, ELS from certain regions, such as American Pima, have superb fiber qualities compared to *G. barbadense* grown in other regions of the world and are heavily promoted and highly sought after by textile manufacturers. Thus, certain ELS cottons from a particular geographical region are more valuable than others. All ELS cotton cultivars are within the *G. barbadense* species, and there is really no physical measurement(s) which can readily distinguish between various ELS cotton cultivars produced from different geographical regions.

Unfortunately, once cotton fibers are processed and made into yarn and/or fabrics, there is no reliable method to determine the origin or cultivar of the fibers utilized to produce the yarn or textile(s). Forging clothing or producing knock-off textile items is a serious problem for the textile industry, costing manufacturers and retail stores millions and perhaps billions of dollars annually, in the United States alone. Some manufacturers are using inferior quality cotton or other cheaper ELS cotton to cut costs. This is not necessarily equivalent to making fake products, but this practice still impacts not only the brand owner but also the cotton producers. Being able to identify the cultivar of a particular species of cotton utilized in a textile item would not only be a way to authenticate an item as legitimate and being made with the type of cotton specified by the owners, but would also enable the detection of forged or counterfeit textile products.

There have been many studies trying to manipulate cotton genes for fiber quality improvement (U.S. Pat. Nos. 6,169,174; 7,060,874; and 6,995,256), enhanced pesticide toxin production (U.S. Pat. Nos. 6,686,149; 6,140,075; and 6,057,370), and herbicide resistance (U.S. Pat. No. 7,223,906). There have also been studies investigating the genetic polymorphism of various cotton species using PCR-based markers (J. Applied Sci. Res. 3(10)1156-1169, 2007). A variety of studies have demonstrated that DNA heterogeneity within strains of similar species can arise both in intragenic (inside) and intergenic (outside) genetic coding regions, and that polymorphism at the level of DNA yields a remarkably specific signature for individuals, strains and species. However, no success has been found in the categorization of cotton cultivars using genetic markers on mature cotton fibers mainly because of the lack efficient primers to amplify fragmented DNA in mature cotton fibers.

SUMMARY

Methods for authenticating articles of manufacture containing mature cotton fibers such as garments or other textile goods are described. Higher quality cotton textile goods are typically made from cultivars of high quality *Gossypium barbadense*. Counterfeit and/or substandard high end textile goods are often made with different cotton cultivars than the cotton cultivar specified by the owners of the textile brand, such as using the locally produced cheaper ELS cultivar instead of imported and more expensive American Pima in some foreign textile mills. When the cotton cultivar in an original textile article is known, the detection of a different cultivar of cotton in the textile articles subsequent to manufacture will indicate that a counterfeit article has been substituted. The methods provide a means for identifying the cotton cultivar in a textile item from a sample of mature cotton fibers taken from the textile item, and for authenticating the textile items based on the identification of the cotton cultivar and species. The authentication can be carried out at different points along the supply or commerce chain between manufacture and retail sale to identify the point in the chain at which counterfeit goods are introduced.

In one embodiment, the method for identifying cotton cultivar comprises collecting mature cotton fibers from a sample, extracting genomic DNA from the collected mature cotton fibers, amplifying the DNA with PCR-based techniques, and analyzing the amplified product to distinguish between a first cotton cultivar and a second cotton cultivar. In the illustrative embodiment the first cotton cultivar is a first *G. barbadense* cultivar and the second cotton cultivar is a second *G. barbadense* cultivar. In other embodiments the sample is a textile item while in other embodiment the sample is raw cotton material.

In certain embodiments, the amplifying further comprises using at least one set of specific primers which target sequence polymorphism between the first cotton cultivar and the second cotton cultivar. In most embodiments, the amplifying comprises at least one set of specific primers which target sequence polymorphism among *G. barbadense* cultivars. In some embodiments, the genomic DNA extracted from the mature cotton fibers originating from the textile in question comprises chloroplast DNA and in other embodiments it comprises nuclear DNA.

In certain embodiments, the targeted sequences of the first cotton cultivar and the second cotton cultivar have different detectable physical characteristics. In other embodiments, the detectable physical characteristic of the targeted sequence is a difference in sequence length for the first cotton cultivar compared to the second cotton cultivar. In some other embodiments, the detectable physical characteristic of the targeted sequence is a different sequence composition for the first and second cotton cultivars. In still other embodiments, the detectable physical characteristic of the targeted sequence is a different sequence composition for the first and second cotton cultivars.

In most embodiments the analyzing of the amplified products comprises detecting the size of the amplified products by capillary electrophoresis. In other embodiments gel electrophoresis may be utilized instead of capillary electrophoresis.

One embodiment of the methods for verifying a textile article comprising collecting cotton fibers from a textile item, extracting genomic DNA from the cotton fibers collected, amplifying said DNA with PCR-based techniques, analyzing the amplified product to distinguish between a first cotton cultivar and a second cotton cultivar, identifying the cotton fibers from the textile item as belonging to the first cotton cultivar or to the second cotton cultivar, and determining from the identified cotton cultivar if the textile article is authentic.

In some embodiments for verifying a textile article, the first cotton cultivar is a G. barbadense cultivar and the second cotton cultivar is a G. hirsutum cultivar.

In yet other embodiments for verifying a textile article, the first cotton cultivar is a first G. barbadense cultivar and the second cotton cultivar is a second G. barbadense cultivar.

In some embodiments for verifying a textile article, the amplifying further comprises using at least one set of specific primers which target sequence polymorphism between the first cotton cultivar and the second cotton cultivar. Also, the targeted sequences of the first cotton cultivar and the second cotton cultivar have different detectable physical characteristics. The detectable physical characteristic can be a difference in length of the targeted sequence when comparing the first and second cotton cultivar to one another. The detectable physical characteristic can also be a slight variation in sequence composition.

In one embodiment of a kit useful for carrying out the methods described herein, the kit comprises a sample collection tube for placing mature cotton fibers obtained from the textile item, a DNA extraction solution, at least one set of specific primers specific for a target sequence found in a first cotton cultivar and a second cotton cultivar, and a PCR amplification buffer solution.

In some embodiments the kit for determining the cotton cultivar of a sample or item further comprises a PCR instrument.

In yet other embodiments, the kit may further be found comprising an internal control for comparing the size of the amplified product.

In certain embodiments, the kit comprises a capillary electrophoresis device.

All patents and publications identified herein are incorporated herein by reference in their entirety.

DESCRIPTION

Definitions

Figure 1:
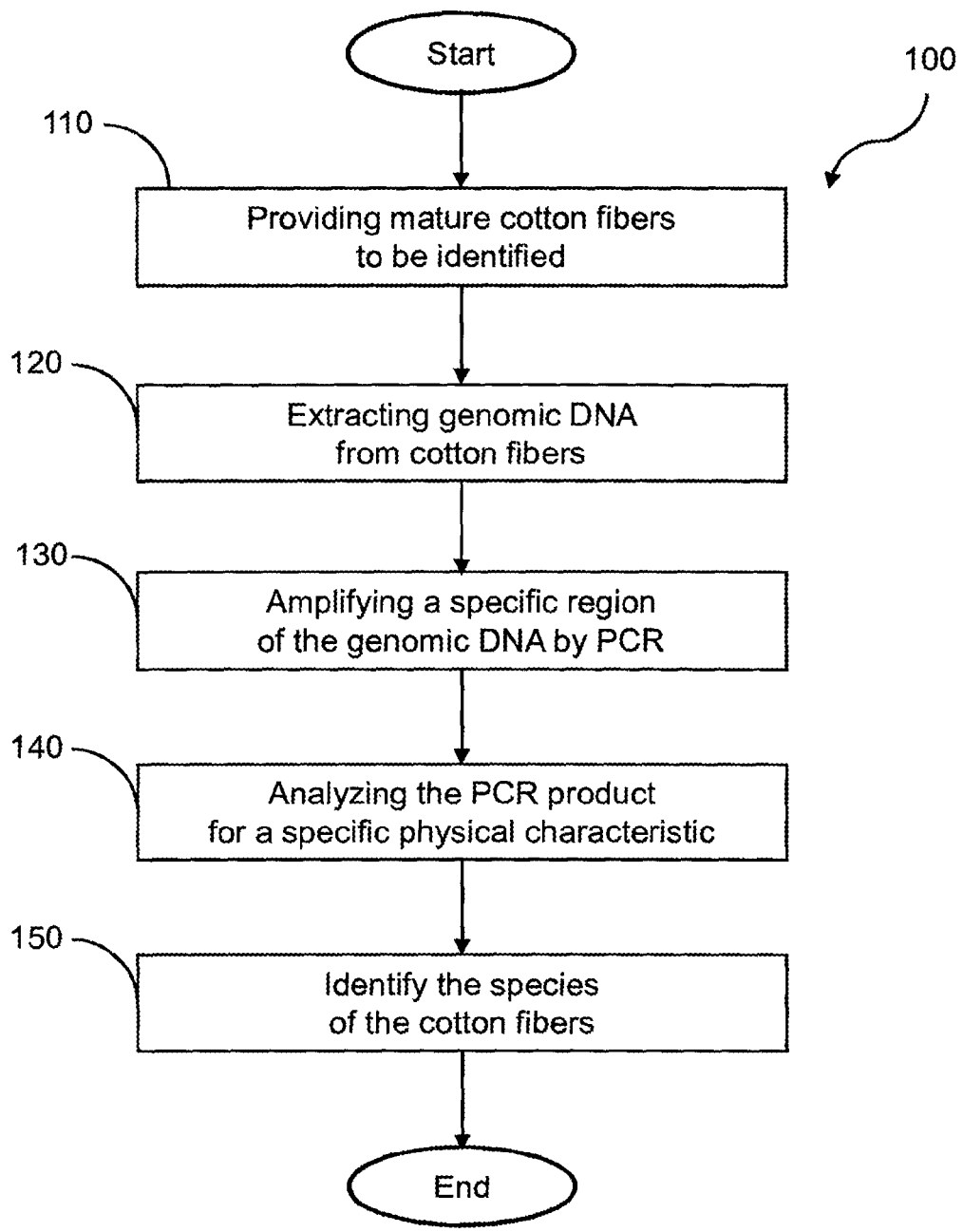
FIG. 1 is a flow chart of one embodiment of the methods for identifying the cotton cultivar of mature cotton fibers.

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Optional" or "optionally" means that the subsequently described event or circumstance may occur but need not occur, and that the description includes instances where the event or circumstance occurs and instances in which it does not.

The terms "those defined above" and "those defined herein" when referring to a variable incorporates by reference the broad definition of the variable as well as preferred, more preferred and most preferred definitions, if any.

The term "ELS" means "extra long staple" cotton fibers. For example, those fibers produced from G. barbadense are ELS cotton fibers.

The term "cultivar" means a cultivated plant that has been selected and given a unique name because it has desirable characteristics that distinguish it from otherwise similar plants of the same species. Cultivar may also mean "sub-species."

The term "genotype" means the unique genetic characteristics of a particular species or cultivar. Genotyping is considered the detection of a particular genotype of a species or sub-species.

The term "Upland fiber" defines cotton fibers which are shorter than ELS cotton fibers. For example, upland fibers are produced from G. hirsutum.

The term "genomic DNA" means the full complement of DNA contained in the genome of a cell or organism. This includes nuclear DNA as well as DNA stored within organelles, such as the mitochondrial genome (mDNA) and the chloroplast genome (cpDNA).

The term "variable region" means a genetic region of similar cotton species which has sequence variation between cultivars or species. The variation may be for example, a difference in sequence length within a genetic region, or single nucleotide changes within a specific genetic region.

The term "variable length polymorphism" means a variety of sequence lengths have been identified or detected for a targeted region across various cotton species or sub-species, such as cultivars.

The term "primer" means an oligonucleotide with a specific nucleotide sequence which is sufficiently complimentary to a particular sequence of a target DNA molecule, such that the primer specifically hybridizes to the target DNA molecule.

The term "probe" refers to a binding component which binds preferentially to one or more targets (e.g., antigenic epitopes, polynucleotide sequences, macromolecular receptors) with an affinity sufficient to permit discrimination of labeled probe bound to target from nonspecifically bound labeled probe (i.e., background).

The term "probe polynucleotide" means a polynucleotide that specifically hybridizes to a predetermined target polynucleotide.

The term "oligomer" refers to a chemical entity that contains a plurality of monomers. As used herein, the terms "oligomer" and "polymer" are used interchangeably.

Examples of oligomers and polymers include polydeoxyribonucleotides (DNA), polyribonucleotides (RNA), other polynucleotides which are C-glycosides of a purine or pyrimidine base, polypeptides (proteins), polysaccharides (starches, or polysugars), and other chemical entities that contain repeating units of like chemical structure.

The term "PCR" refers to polymerase chain reaction. This refers to any technology where a nucleotide is amplified via temperature cycling techniques in the presence of a nucleotide polymerase, preferably a DNA polymerase. This includes but is not limited to real-time PCR technology, reverse transcriptase-PCR, touchdown PCR and standard PCR methods.

The term "nucleic acid" means a polymer composed of nucleotides, e.g. deoxyribonucleotides or ribonucleotides, or compounds produced synthetically which can hybridize with naturally occurring nucleic acids in a sequence specific manner analogous to that of two naturally occurring nucleic acids, i.e., can participate in hybridization reactions, e.g., cooperative interactions through Pi electron stacking and hydrogen bonds, such as Watson-Crick base pairing interactions, Wobble interactions, etc.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "polynucleotide" refers to a single or double stranded polymer composed of nucleotide monomers of generally greater than 50 nucleotides in length.

The term "monomer" as used herein refers to a chemical entity that can be covalently linked to one or more other such entities to form an oligomer. Examples of "monomers" include nucleotides, amino acids, saccharides, peptides, and the like.

The term "identifiable sequence" or "detectable sequence" means a nucleotide sequence which can by detected by hybridization and/or PCR technology by a primer or probe designed for specific interaction with the target nucleotide sequence to be identified. The interaction of the target nucleotide sequence with the specific probe or primer can be detected by optical and/or visual means to determine the presence of the target nucleotide sequence.

In general, the term "textile" may be used to refer to fibers, yarns, or fabrics. More particularly, the term "textile" as used herein refers to raw cotton, ginned cotton, cotton fibers, cotton yarns, cotton fabrics, yarn that is blended with cotton, fabric that is blended with cotton, or any combination thereof.

The term "mature cotton fiber" as used herein refers to a cotton fiber having a lumen wall that separates the secondary wall (consisting of cellulose) from the lumen that has naturally collapsed. The lumen is the hollow canal that runs the length of the fiber and is filled with living protoplast during the growth period; after the fiber matures and the boll opens the protoplast dries up and the lumen will naturally collapse and leave a large central void in each fiber.

The present specification describes methods for identifying and verifying a cultivar of a particular cotton species using mature cotton fibers. Being able to determine the particular cultivar of a cotton shipment or textile allows for the quality of the cotton to be verified, which aids in protecting the reputation of high end textile brands.

In particular, the methods relate to verifying the type/cultivar of cotton used in the manufacturing of an article comprising cotton. There are four major cotton species utilized in textiles around the globe, and they are G. barbadense, G. hirsutum, G. arboreum, and G. herbaceum. Each one of these cotton species has a plurality of cultivars, and the cultivars from a particular species can vary considerably in quality. The methods allow for the identification and distinction of one cultivar from other cultivars of the same species. The present methods allow for cultivar genotyping of a wide range of cotton species. The cotton species mentioned herein are only exemplary and should not be taken as limiting.

Most of the cotton textiles produced are made from two cotton species, G. barbadense and G. hirsutum, and both of these species comprise a plurality of cultivars, each cultivar having unique genotypic and phenotypic properties from one another. Methods are provided for identifying "Extra Long Staple" (ELS) cottons or cultivars of G. barbadense grown from different geographical regions of the world. Methods are also provided for identifying Upland cottons or cultivars of G. hirsutum as well as other Upland species grown from different geographical regions of the world.

The methods allow a user to genetically identify textiles made of cotton fibers from a particular cotton cultivar. The process involves extracting DNA from mature cotton fibers or textiles and amplifying DNA using specific primers and the Polymerase Chain Reaction (PCR) method. Specific primers targeting regions exhibiting sequence variation or sequence polymorphism among Gossypium cultivars were used to distinguish various types of cultivars.

There are subtle genetic variations in the genetic makeup of the G. barbadense/ELS cultivars. The methods provide genetic tests which definitively identify fibers and textiles as being made from a particular ELS cultivar. The methods utilize at least one variable sequence region found within the cotton genomes of interest, which allows the cotton cultivars to be distinguished from one another. In general, to identify cotton fibers originated from a particular cultivar, endogenous genetic markers based on the genetic variation between the cultivars of interest were utilized.

A variable region can differ in either DNA length or DNA sequence, while the non-variable regions have identical DNA sequences between the cultivars being compared. Thus, the variable region can be utilized as an endogenous marker to distinguish between ELS cotton cultivars. By targeting regions of the DNA genome(s), which have sequence variations the mature cotton fibers can be identified as a specific cotton cultivar by the length or size of the target sequence(s). To genotype ELS cotton cultivars, several variable sequence regions within the cotton genome which identify different ELS cottons were utilized. The method allows for cotton sequence-specific primers associated with simple sequence repeats (SSRs) to be used for ELS cultivar differentiation. This allows the use of SSR primers to detect endogenous markers with varying DNA length polymorphisms between the different cultivars.

While sequence length is the physical characteristic targeted by the endogenous marker the physical characteristic used to identify the cotton fibers as a particular ELS cultivar could be differences in site specific mutations which can be detected by specific probes designed for each cotton cultivar of interest.

Generally, ELS sequence-specific primers associated with simple sequence repeats (SSRs) are used to amplify DNA from mature cotton fibers or textiles and DNA variable length polymorphism (genotyping) was used to distinguish different ELS cultivars. When multiple primers are used, they create a powerful genotyping tool that is capable of discriminating thousands of ELS cultivars. The process involves extracting DNA from mature cotton fibers or textiles and amplifying DNA using PCR methods. Specific primer sets targeting regions exhibiting sequence variation or sequence polymorphism among different ELS cultivars are used to identify individual ELS cultivars. PCR results were analyzed by capillary electrophoresis for DNA length polymorphism, and results from multiple primers sets created a unique genotype for individual ELS cultivars.

By testing all available ELS cultivars using the methods described herein, an ELS identity gene bank can be established and each ELS cultivar can be associated with a unique DNA genotype.

DNA fragment size was determined by an internal size standard using best-fit second order curve interpolation; therefore, DNA sequence lengths from different runs are considered to have the same genotype if the variation is within one base pair. Each SSR primer set generates multiple DNA sequence lengths for each ELS cultivar. The multiple DNA length products produced in the cultivars is due to ELS cotton species being tetraploid, i.e. having a possibility of four different chromosomal sets. The methods demonstrate that a combination of primer sets can discriminate between thousands of different cultivars.

In other embodiments, SNP or haplotyping are utilized to distinguish different cotton cultivars. Primers are designed to amplify DNA fragments containing SNP/haplotypes and then the amplified DNA fragments are analyzed by sequencing. SNP analysis kits are available, such as the TaqMan™ kit by ABI, or SNP analysis can be carried out by a synthesis method, such as Pyrosequencing™.

FIG. 1 is a flow chart illustrating one embodiment of a method 100 for identifying the cultivars of mature cotton fibers. At event 110, mature cotton fibers are collected and/or obtained from a cotton source. The cotton source may be raw cotton fibers from a specific geographical location, from a cotton textile, from a cotton textile article or garment, or from a source were the cotton cultivar is already known. The cotton fibers may also be from anthropological textiles as well as fibers from artwork canvases or any other article where knowing the cotton cultivar utilized for an article would be advantageous in verifying or authenticating the item. The methods allow for verification of articles in a manner that helps prevent forgers and counterfeiters from substituting false or counterfeit goods in place of authentic items.

At event 120, the method 100 further comprises extracting genomic DNA from the collected cotton fibers. In general, a variety of nucleic acid extraction solutions have been developed over the years for extracting nucleic acid sequences from a sample of interest. See, for example, Sambrook et al. (Eds.) *Molecular Cloning*, Cold Spring Harbor Press, 1999. Many such methods typically require, for example, a detergent-mediated step, a proteinase treatment step, a phenol and/or chloroform extraction step, and/or an alcohol precipitation step. Some nucleic acid extraction solutions may comprise an ethylene glycol-type reagent or an ethylene glycol derivative to increase the efficiency of nucleic acid extraction while other methods use only grinding and/or boiling the sample in water. Other methods, including solvent-based systems and sonication, could also be utilized in conjunction with other extraction methods.

In most embodiments, about 5 mg to about 30 mg of cotton fiber or cotton lint, and in certain instances between about 10 mg to about 15 mg of cotton fibers are needed for sufficient DNA to be extracted from the sample for analysis. DNA extraction protocols are derived from standard molecular biology DNA extraction procedures, which can be easily accomplished by people skilled in the art.

While extracting DNA from seeds and leaves from various cotton species is quite common for cotton research genomics, utilizing DNA from the mature cotton fibers is quite unusual and unique. The amount of DNA as well as the integrity of the DNA isolated from mature cotton fibers may not be adequate for researching genetic variability and relationships among a plurality of genotypes or cotton cultivars. The use of cotton fibers as a DNA source as described herein is, surprisingly, sufficient for identifying and distinguishing between a plurality of different cotton cultivars. This is partly due to the simplicity of the genetic test preformed in the methods.

The embodiment of FIG. 1, in event 130, further comprises amplifying a target sequence or specific DNA region of the cotton DNA genome extracted from the cotton fibers in event 120. Polymerase Chain Reaction procedures enables the target sequence within the cotton cultivar genome to be amplified, or copied, to a detectable quantity. In general, amplification comprises temperature cycling of the genomic DNA sample in the presence of free nucleotides, a specific set of primers for the target DNA, along with a polymerase which allows the target DNA to be copied, i.e. amplified.

Utilizing primer software known to those skilled in the art, a plurality of primers were identified and designed for the selected variable region(s) of the cotton cultivar DNA sequences, allowing for the amplified PCR product(s) to be identified as being from a particular cultivar of particular *Gossypium* cotton species. PCR primers were designed according to known criteria and PCR procedures may be conducted in commercially available instruments. Primers were designed to distinguish between the targeted sequences of the cultivars by exploiting the differences in at least one physical characteristic related to the targeted sequences. The "physical characteristic" utilized to distinguish between the cotton cultivars is either a detectable difference in length/size of the targeted sequence or a detectable DNA sequence variation (i.e. base substitution) specific for each of cotton cultivars being analyzed.

Generally the primers designed for PCR amplification in event 130 utilize simple sequence repeats (SSR) or microsatellites which are polymorphic loci present in nuclear and organellar DNA (i.e. chloroplast DNA). Identifying regions comprising SSRs enables one set of primers to amplify a target sequence in a plurality of cultivars of a particular *Gossypium* cotton species, with the target sequences from one cultivar to another being different in length due the presence of varying number of SSRs found in the target sequence.

In most embodiments, when a large number of cultivars need to be distinguished from one another, more than one primer set is utilized in the methods. The number of primer sets needed to identify a particular cultivar is dependent on the number of possible cultivars that the sample may be from. When there are only two cultivar possibilities for the sample, one primer set may be all that is needed to distinguish between the two cultivars. When there are a multitude of possible cultivars that the sample may have originated from, about two to about seven primer sets may be utilized to analyze the cotton fiber sample. In Example 2 below, five primer sets were utilized to distinguish between the genotypes of 25 cultivars of *G. barbadense*. The range of primers set utilized in the methods are from about one primer set to about ten prime sets, more likely from about two primer sets to about seven primer sets, and even more likely from about three primer sets to about five primer sets.

In some embodiments, nested set primers are utilized to achieve appropriate amplification of the targeted variable region(s) of the cotton cultivars of interest. Again, these nested set primers were identified and designed utilizing primer software and the genomic sequences of the cotton cultivar of interest using primer design methods known to those skilled in the art of primer design.

Examples of primers utilized in some of the embodiments of the methods are given below. The primer sequences given below are only exemplary and are not meant to be limiting in the scope for distinguishing or verifying cotton fibers as being from a unique pima cultivar As exemplified by 14 different genotypes in Table 1, cultivars Cobalt and PO3X8161 share 8 genotypes but differ in 6 genotypes. Among 5 primers, ELS24 and ELS29 amplify the same genotypes for both cultivars, and it is the remaining three primer sets that distinguish the Cobalt cultivar from the PO3X8161 cultivar.

While the above example utilizes a variable region within an intron, it is also possible to utilize a variable region found within an exon or gene region. The targeted marker or sequence is also not limited to a variable region found in chloroplast DNA, but may also be located in nuclear genomic DNA, as well as mitochondrial DNA.

The method 100 illustrated in FIG. 1 further comprises analyzing the PCR product(s) for a specific physical characteristic profile related to only one of the cotton cultivars of interest in event 140. When the identifying physical characteristic profile is the length or size of the PCR products produced in event 130, techniques which allow for efficient size differentiation between the PCR products produced by one cotton cultivar over another are utilized.

With capillary electrophoresis, it is possible to distinguish between the varying sizes of the PCR products produced by DNA from mature cotton fibers of *G. barbadense* cultivars. For example, when utilizing primer set ELS91 for PCR amplification, the PCR products produced by *G. barbadense* cultivars ELS Colbalt and ELS PO3X8161 (see Table 1), can be distinguished by capillary electrophoresis. Utilizing an internal standard of known size in the capillary electrophoresis experiments enables the lengths (e.g. number of base pairs) of the PCR products of each cultivar to be determined and the profiles compared to one another. The variable amplicon lengths produced by cultivar Colbalt with the ELS91 primers are 102, 276 and 309. The variable amplicon lengths produced by cultivar PO3X8161 by the ELS91 primer set are 267, 308 and 314 base pairs in length, which is a distinctly different pattern of PCR amplicon products than those produced by the Colbalt cultivar. Thus the two cultivars can be uniquely identified from one another using the methods.

In most embodiments, where the physical characteristic of the PCR products being analyzed in event 140 is size/length, a capillary electrophoresis device such as an AB1310 genetic analyzer can be utilized to determine the size of the PCR product(s) produced. For capillary electrophoresis, the length of the DNA amplicons produced by PCR is determined by extrapolating size data from an internal control run with the sample of known size. This allows for the capillary electrophoresis results of multiple PCR experiments, each with a different set of primers, to be overlaid to provide a variable amplicon length polymorphism (VALP) profile for each cultivar of interest. See example 1 and 2, below.

In general, the size resolution of the capillary electrophoresis is capable of distinguishing between amplicons which differ by only about 2 base pairs. The sensitivity of capillary electrophoresis enables in some embodiments the use of primers which target variable regions of the cotton cultivar where the difference between the size of a first cultivar amplicon and a second cultivar amplicon is less than about 10 base pairs but greater than about 2 base pairs, and in some embodiments the size difference can be less than about 6 base pairs but greater than about 3 base pairs. In an even broader embodiment, the size can range from 1 base pair to 60 base pairs.

In event 150, the cultivar of the analyzed cotton fibers is determined. This determination can be made by comparing the identified VALP profile of the PCR products produced by the sample to the theoretical and actual known sizes of the targeted and amplified sequences for specified *G. barbadense* cultivars in event 150. The VALP profiles of various cultivars may be comprised in a data base or cotton cultivar VALP genotype bank which the VALP results obtained from the sample can be compared to and aid in cultivar identification.

The PCR products from known *G. barbadense* cultivars may also be run on a gel during electrophoresis to determine a VALP profile for the cotton sample and aid in identifying the cultivar from which the sample originated. Once the lengths of the PCR products has been determined by either gel electrophoresis, capillary electrophoresis or other similar DNA sizing techniques, the analyzed sample can be identified and confirmed as a particular cotton cultivar 150.

In other embodiments, the physical characteristic being analyzed is not length but a DNA sequence specific to a particular cultivar. In this situation, PCR amplification may be performed in the presence of a non-primer detectable probe which specifically binds the PCR amplification product produced by one cultivar and not by other cultivars. PCR primers are designed according to known criteria and PCR may be conducted in commercially available instruments. The probe is preferably a DNA oligonucleotide specifically designed to bind to the amplified PCR product. The probe preferably has a 5' reporter dye and a downstream 3' quencher dye covalently bonded to the probe which allows fluorescent resonance energy transfer. Suitable fluorescent reporter dyes include 6-carboxy-fluorescein (FAM), tetrachloro-6-carboxy-fluorescein (TET), 2,7-dimethoxy-4,5-dichloro-6-carboxy-fluorescein (JOE) and hexachloro-6-carboxy-fluorescein (HEX). A suitable reporter dye is 6-carboxy-tetramethyl-rhodamine (TAMRA). These dyes are commercially available from Perkin-Elmer, Philadelphia, Pa. Detection of the PCR amplification product may occur at each PCR amplification cycle. At any given cycle during the PCR amplification, the amount of PCR product is proportional to the initial number of template copies. The number of template copies is detectable by fluorescence of the reporter dye. When the probe is intact, the reporter dye is in proximity to the quencher dye which suppresses the reporter fluorescence. During PCR, the DNA polymerase cleaves the probe in the 5'-3' direction separating the reporter dye from the quencher dye increasing the fluorescence of the reporter dye which is no longer in proximity to the quencher dye. The increase in fluorescence is measured and is directly proportional to the amplification during PCR. This detection system is now commercially available as the TaqMan® PCR system from Perkin-Elmer, which allows real time PCR detection.

A probe specific for a first *G. barbadense* cultivar PCR product may be analyzed in the same or a separate PCR sample tube as the probe specific for a second *G. barbadense* cultivar PCR product. Utilizing real-time PCR, the signal from a probe corresponding to a specific cotton cultivar will identify which cotton cultivar has been collected. It is also possible to attached unique probes for each cultivar to a micro-array and test the sample for a plurality of cultivars utilizing micro-array technology.

Figure 2:
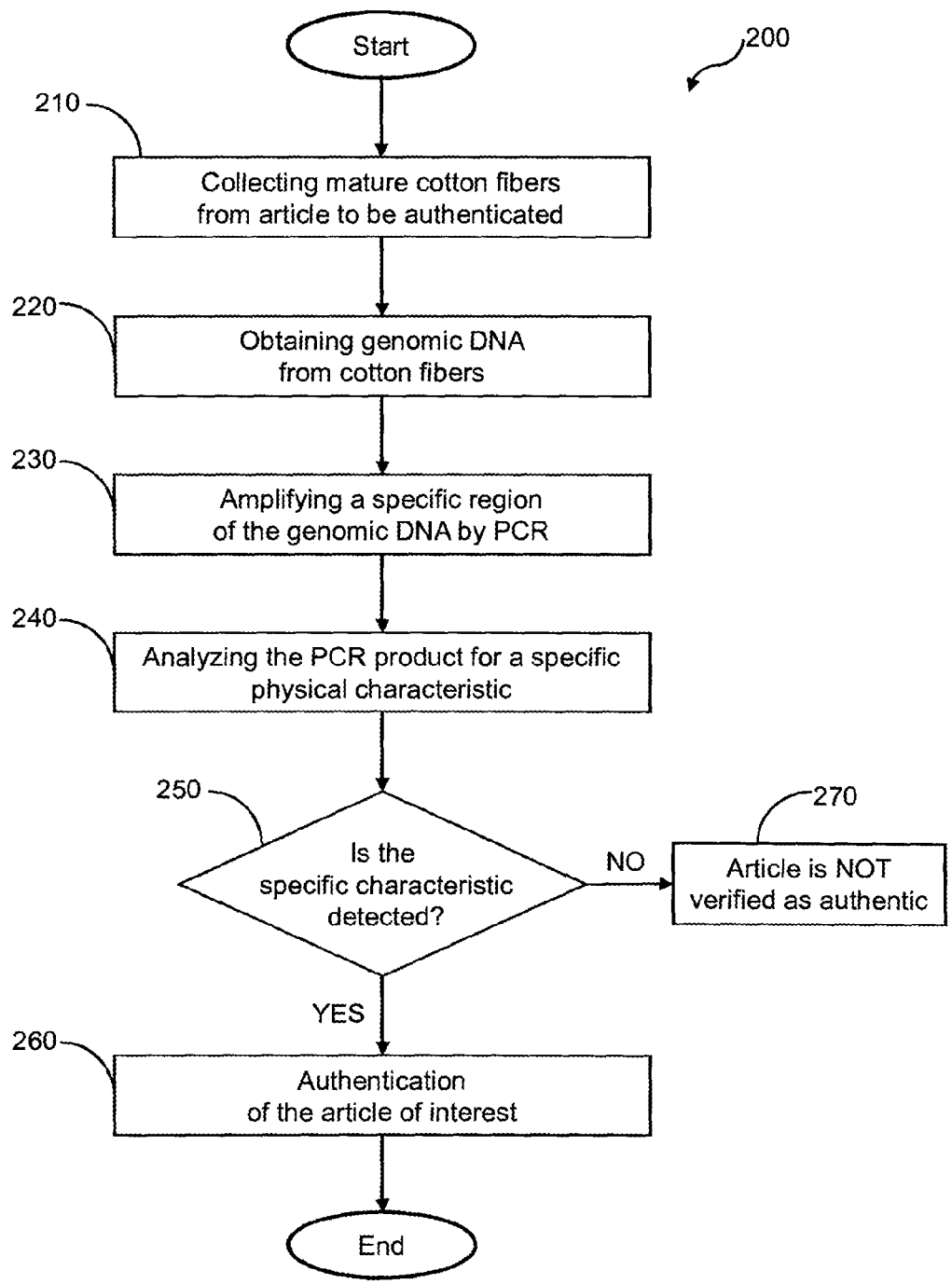
FIG. 2 is a flow chart of one embodiment of the methods for authenticating an article.

FIG. 2 is a flow chart illustrating generally a method 200 for authenticating or identifying an article as being manufactured with a specified cotton cultivar. Usually verifying or authenticating an article occurs after the article has been introduced into a supply chain. Frequently, counterfeiters and forgers have the best access to articles after they are being shipped from the manufacturer/producer to wholesale or retail outlets or locations. With the methods described herein, a producer can track and authenticate articles or goods, allowing for better monitoring of when and where counterfeit goods are being replaced with forgeries or otherwise altered. When the article has entered a supply chain, a manufacturer or an authorized individual can collect a sample from the article at any desired point along the supply chain for authentication purposes.

The method 200 comprises, at event 210, collecting mature cotton fibers from an article to be authenticated. Collecting a sample may involve scraping, cutting or dissolving a portion of the article, to obtain a cotton fiber sample for analysis. The collecting of the sample may be carried out, for example, by cutting the article to remove mature cotton fibers from the article. The sample collecting in other embodiments may be achieved by tweezing, scraping, or abrading the article with appropriate sampling tools configured to remove a sufficient amount of cotton fibers or cotton lint for analysis. Collecting fiber samples may, for example, occur at any point along the supply or commerce chain where there is concern about or risk of introduction of counterfeit articles.

The method 200 for authenticating an article further comprises, in event 220, obtaining or extracting genomic DNA from the collected cotton fibers. Extraction, isolation or purification of the genomic DNA obtained in the sample may be required. A variety of nucleic acid extraction solutions have been developed over the years for extracting nucleic acid sequences from a sample of interest. See, for example, Sambrook et al. (Eds.) *Molecular Cloning*, Cold Spring Harbor Press, 1999. Many such methods typically require one or more steps of, for example, a detergent-mediated step, a proteinase treatment step, a phenol and/or chloroform extraction step, and/or an alcohol precipitation step. Some nucleic acid extraction solutions may comprise an ethylene glycol-type reagent or an ethylene glycol derivative to increase the efficiency of nucleic acid extraction while other methods only use grinding and/or boiling the sample in water. Other methods, including solvent-based systems and sonication, could also be utilized in conjunction with other extraction methods.

The authentication method 200 further comprises, in event 230, amplifying at least one specific region of the extracted genomic DNA by PCR based techniques. The procedures and techniques for PCR amplification of a targeted sequence are similar to those described above in the methods illustrated in FIG. 1. There are numerous cultivars of each of the species *G. barbadense* and *G. hirsutum* which are utilized in the manufacturing of cotton textiles worldwide. The primers designed and selected in many embodiments enable a user to distinguish between the cultivars of *G. barbadense*. It should be noted that other cultivars from various cotton species ELS or Upland, and in particular *G. hirsutum*, can also be identified using the methods described herein. In other embodiments primers may be selected and used for distinguishing cultivars from different cotton species. The use of cultivars from the *G. barbadense* species within the specification is only exemplary and should not be interpreted as limiting in scope to the species or cultivars which can be identified using the methods described herein.

The method 200 for authenticating an article further comprises, in event 240, analyzing the PCR product(s) for a specific physical characteristic or specific physical characteristic profile, such as length of the PCR product(s) or a specific DNA sequence associated with a specific cotton cultivar (e.g. *G. barbadense*). Analyzing the PCR product produced is generally the same as described above in the methods illustrated in FIG. 1. Numerous ELS cultivars have been shown to produce the identical or very similar length PCR products, which are easily identifiable as *G. barbadense* and are distinguishable from various Upland cultivars of *G. hirsutum*. In general, to distinguish between cultivars of a particular species, a plurality of primers sets are utilized to obtain a variable amplicon length polymorphism (VALP) profile for each cultivar of interest. Example 1 and Example 2 below describe the identification or VALP profile results of various cultivars in more detail. When the aim is to authenticate a cotton textile as being a specific *G. barbadense* cultivar, the analysis of the sample can be simplified to utilize the least number of primer sets which will determine if the samples in question have the associated VALP to the cultivar of interest. In many instances, a textile shipment may be on a stringent time table and a quick but accurate test is required, thus limiting the amount of time to perform the analysis is preferred. Utilizing only those primer sets which are needed to produce a particular cultivar's VALP profile fulfills the desire for a quick and reliable verification test.

In event 250, the results of the analysis of the collected sample are reviewed and a query or determination is made as to whether or not a physical characteristic (i.e. known PCR product length) or the VALP profile for a particular cultivar was detected in the sample. If the physical characteristics associated with a particular cotton cultivar nucleic acid is not found or not detected in the collected sample of the textile article at event 250, the conclusion at event 270 from the analysis is the that article is not made from that particular cotton cultivar and may have been tampered with or substituted. If the physical characteristic and/or VALP profile associated with the cotton cultivar is detected in the sample at event 250, then the article is verified in event 260 as being authentic.

If a determination is made in event 270 that an article is not authentic, a different, earlier point in the supply or commerce chain may be selected and events 210 through 250 may be repeated. Thus an article from an earlier point in the supply chain would be selected, cotton fibers collected, and analyzed. If it is again determined that the article is not authentic or has been otherwise tampered with, then events 210-250 may be repeated with an article selected from yet an earlier point in the supply chain. In this manner, the time and/or location of tampering or counterfeit substitution of the textile article may be located.

The method also provides kits for verifying cotton fibers and authenticating articles of interest using the methods and kit. The kits may comprise, for example, a container of the nucleic acid extraction buffer, and a sample tube for holding a collected mature cotton fiber sample of the item or article to be authenticated. The kits may include at least one primer set configured to produce amplified PCR fragments from a plurality of cultivars (e.g. cultivars of *G. barbadense* species). The kits may further comprise a collection tool for taking a sample of the labeled article for transfer to the sample tube. The kits may also include a portable electrophoretic device (e.g. gel apparatus or capillary electrophoresis system) for analyzing PCR products. The kits may still further comprise an internal control for fragment size comparison for capillary analysis.

By way of example, the collection tool of the kit may comprise a blade or scissors, or the like, for cutting a piece of the article. The sample tube of the kit may comprise a sealable vial or Eppendorf tube, and may contain solvent or solution for extraction of the nucleic acids (e.g. DNA) from the sample taken from the textile article.

The kit may further comprise primers and/or probes as well as solutions appropriate for PCR analysis. The kit may further comprise a small PCR instrument for analysis of the extracted nucleic acids from the mature cotton fibers.

The capillary electrophoresis device of the kit may comprise an internal control for detecting the fragment size of the amplified PCR product(s).

In many embodiments, the kit will further comprise a system for accessing a data base of the genotypes (i.e. VALP profiles) of cultivars of interest, for comparison to the results obtained from the cotton fiber sample.

The illustrative kits thus provide a convenient, portable system for practicing the methods described herein.

Illustrative methods for authenticating textile articles utilizing mature cotton fibers are provided in the following Examples.

EXAMPLES

The following preparations and examples are given to enable those skilled in the art to more clearly understand and to practice the present methods. They should not be considered as limiting the scope, but merely as being illustrative and representative thereof.

Example I

Genotyping ELS cultivars with mature cotton fibers. Two ELS cultivars were analyzed to identify unique variable amplicon length polymorphisms between the two cultivars using the methods.

For DNA extraction, 10-15 mg of mature cotton fibers were weighed and put into 1.5 ml Eppendorf tubes. DNA extraction protocols are derived from standard molecular biology DNA extraction procedures, which can be easily accomplished by people skilled in the art. Sample tubes were then vortexed and centrifuged briefly to be used as PCR templates. For DNA amplification, a PCR master mix containing 10 ul of amplification buffer, 0.5 ul of 10 uM forward and reverse primers, 5 ul of water, and 4 ul of DNA extracts were put into 0.2 ml thin wall PCR tubes and run for 40 cycles for DNA amplification. PCR anneal temperature and duration times were adjusted according to individual primer sets, and any one familiar in the art of PCR will be able to design their own scheme.

Multiple primer sets were used to produce a plurality of PCR amplicons for each cultivar, the various PCR amplicons representing the unique genetic make-up of each cultivar. Those with ordinary skill in the art of designing primer sets would be able to produce a plurality of different primer sets other than those described herein, which can distinguish between the ELS cultivars, given the genomic sequences of *G. barbadense* (GenBank Accession. No. NC_008641) and *G. hirsutum* (GenBank Accession No. NC_007944). These specific primers are merely exemplary.

While the primer sets in this example were utilized separately in individual PCR sample tubes, a multiplex of primer sets could be used in one PCR sample tube to expedite the analysis of the cotton sample. One skilled in the art of primer design would be able to design primer sets capable and appropriate for multiplex PCR without undue experimentation.

The PCR products were analyzed by capillary electrophoresis using an ABI310 genetic analyzer. After running the ELS samples through capillary electrophoresis, sizing data was collected for SSRs primer amplicons. Comparison of the electrograms of the PCR amplicons produced by cotton fiber samples from Cobalt and from PO3X8161 ELS cultivars was carried out. Five primer sets were utilized in this example to produce a plurality of DNA amplicon lengths associated with each cultivar tested.

In general, for each cultivar an electrogram is produced for each primer set, where the X-axis of the electrogram depicts amplicon size in base pairs and the Y-axis depicts fluorescent signal intensity. DNA amplicon size was determined by an internal size standard Liz600 using best-fit second order curve interpolation; therefore, DNA sequence lengths from different runs are considered to have the same genotype if the variation is within one base pair. Each peak on the electrogram represents a PCR amplicon product of a specific length. The electrograms generated from each primer set are overlaid to produce an electrogram with a plurality of peaks representing the variable amplicon length polymorphism profile for each cultivar, related to the 5 primers used. The five SSR primer sets used in this example were ELS24, ELS29, ELS30, ELS35, and ELS91.

Each SSR primer set generated multiple DNA sequence length products for each ELS cultivar. The two ELS cotton cultivars analyzed were shown to possess unique DNA PCR amplicon combinations after being amplified by the different SSR primer sets. A variable amplicon length polymorphism (VALP) profile was generated for each cultivar by combining/overlaying the results derived from the 5 sets of primers. The VALP profile for each cultivar was found to be specific and unique to that cultivar. The variable amplicon length polymorphism identified for these cultivars arises partly from these cotton species being tetraploid.

The differences between the ELS cultivars are more evident when the genotypes (e.g. the variable amplicon length polymorphism associated with each genotype) are compared by base pair length. Table 1, shows the comparison of the genotypes between ELS cultivars Cobalt and PO3X8161. Table 1 shows that each cultivar contains 13 variable length PCR products as generated by 5 different SSR primer sets. PCR products are considered to be from the same target sequence when the size variation is within one base pair. Table 1 shows that there are 7 identical DNA amplicon products shared between the two cultivars (Italic) and 5 different sized DNA amplicons specific to a particular cultivar (bold). Essentially, each ELS cultivar possess unique genotypes, and by comparing various sized PCR products produced by the methods described herein, these two cultivars can be distinguished by the detection of variable amplicon length polymorphism.

TABLE 1

Variable amplicon length polymorphism of Cobalt and PO3X8161 cultivars.

| Primer Sets | Colbalt Cultivar | PO3X8161 Cultivar | Primer sequences | |
|---|---|---|---|---|
| ELS91 | 102.29 | — | ACTTCAAGGAGTCAGATT | SEQ. ID. No. 1 |
| | 267.25 | 267.53 | GCAATCCTCACCGAGATG | SEQ. ID. No. 2 |

TABLE 1-continued

Variable amplicon length polymorphism of Cobalt and PO3X8161 cultivars.

| Primer Sets | Colbalt Cultivar | PO3X8161 Cultivar | Primer sequences | |
|---|---|---|---|---|
| | 309.2 | 308.99 | | |
| | — | 314.3 | | |
| ELS24 | 124.2 | 124 | CCTTTATAATCCCCCATCA | SEQ. ID. No. 3 |
| | 126.6 | 126.7 | GCATCAGAAAAAGTTCAA | SEQ. ID. No. 4 |
| ELS29 | 185.45 | 186.02 | CGCACCACTATCAAATTTC | SEQ. ID. No. 5 |
| | 214 | 215.2 | GCTTTTCGACTTGAGCAAC | SEQ. ID. No. 6 |
| ELS30 | 140.3 | 140 | CCGAAGACAAAGAAACACA | SEQ. ID. No. 7 |
| | 152.8 | — | CGAGATCGCAAAAATGAAG | SEQ. ID. No. 8 |
| | 161.8 | 162.5 | | |
| ELS35 | — | 99.01 | CCAGAAAGAAGAAGGGAAG | SEQ. ID. No. 9 |
| | — | 119.8 | CGTTTTGGAGAAAATGGTCA | SEQ. ID. No. 10 |
| | 140 | — | | |
| | — | 144.6 | | |
| | 164.2 | — | | |
| | — | 166.4 | | |
| | 185.99 | — | | |

This example demonstrates that ELS cotton fibers can be identified and authenticated as a particular cultivar by PCR and capillary electrophoresis techniques. The present example further demonstrates that by utilizing a combination of various primer sets, thousands of different cultivars could be typed and distinguished from one another using the methods.

Example II

Genotyping of 25 ELS cotton cultivars. For DNA extraction, 10-15 mg of mature cotton fibers were weighed and put into 1.5 ml Eppendorf tubes. DNA extraction protocols are derived from standard molecular biology DNA extraction procedures, which can be easily accomplished by people skilled in the art. Sample tubes were then vortexed and centrifuged briefly to be used as PCR templates. For DNA amplification, a PCR master mix containing 10 ul of amplification buffer, 0.5 ul of 10 uM forward and reverse primers, 5 ul of water, and 4 ul of DNA extracts were put into 0.2 ml thin wall PCR tubes and run for 40 cycles for DNA amplification. PCR anneal temperature and time were adjusted according to individual primer sets, and anyone familiar in the art of PCR will be able to design their own scheme. There were multiple primer sets used in the PCR reaction and various PCR amplicons were produced that represented the unique genetic make-up of each cultivar. After that, PCR products were analyzed by capillary electrophoresis using an ABI310 genetic analyzer. After running the ELS samples through capillary electrophoresis, sizing data were collected for SSR primer amplicons for each known cultivar as shown in Table 2. DNA fragment size was determined by an internal size standard Liz600 using best-fit second order curve interpolation; therefore, DNA fragments from different runs are considered to have the same genotype if the variation is within one base pair. Each SSRs primer set generates multiple DNA fragments and a combination of primer sets can discriminate thousands of different cultivars.

TABLE 2

Genotypes of 25 ELS cultivars using 5 ELS sequence specific SSRs primers.

| SUPIMA NAME | ELS91 | | ELS24 | | ELS29 | | ELS30 | | | ELS35 | | |
|---|---|---|---|---|---|---|---|---|---|---|---|---|
| Cobalt | 102.29 | 267.25 | 309.2 | 124.2 126.6 | 185.45 | 214 | 140.3 152.8 161.8 | | 140 | 164.2 185.99 | | |
| DP 340 | 164.99 | 309.04 | 314.7 | 124.2 126.8 | 186.19 | 213.4 | 141.2 152.8 161.8 | | 140.7 | 164.6 186.54 | 250.1 | |
| DP 353 | 267.25 | 309.49 | 315 | 123.9 126.9 | 185.87 | 213.3 | 140.9 162.3 171.6 | | 128.4 | 140 163.4 | — | |
| E-503 | 267.44 | 309.07 | 314.4 | 123.7 126.4 | 186.35 | 213.4 | 140.9 — 162.2 | | 143.8 | 164.2 186.09 | 193.1 | |
| OA 353 EXP | — | 309.04 | 314.6 | 124 126.7 | 186.09 | 215.1 | 140 — 162 | | 140 | 164.4 186.41 | 193.1 | |
| PHY 820 | — | 308.73 | 314.4 | 125.4 128.3 | 186.05 | 215.2 | 140 — 162.4 | | 139.9 | 164.5 176.15 | 186.5 | |
| PHY 830 | — | 308.45 | 314 | 126.4 — | 185.59 | 215.2 | 140 — 162.3 | | 139.9 | 175.8 186.42 | — | |
| PI MIXED | 271.77 | 310.76 | 315 | 123.1 125.9 | 185.7 | 214.2 | — 161.4 | | 139.9 | 164.7 175.7 | 186.4 | |
| PO3X 8161 | 267.53 | 308.99 | 314.3 | 124 126.7 | 186.02 | 215.2 | 140 — 162.5 | | 99.01 | 119.5 144.6 | 166.4 | |
| PHY 800 | 267.51 | 309.22 | 314.6 | 124.1 126.8 | 186.08 | 213.3 | 140 153.3 162.4 | | — | 164.6 186.46 | — | |
| SJV EXP PIMA | — | 309.21 | 314.8 | 124.1 126.7 | 185.94 | 215.2 | 140 153.1 162 | | 140 | 164.6 186.3 | 281.2 | |
| Egyptian Giza 70 | — | 308.86 | 313.9 | 123.8 126.7 | 185.94 | 215.2 | 140 153.5 162.4 | | 163.8 | 186.2 269.59 | 370 | |
| Egyptian Giza 86 | 141.07 | — | — | 124 126.7 | 185.89 | 215.3 | 140 153.2 162 | | 131.9 | 164.2 — | 185.9 | |
| Egyptian Giza 88 | 103.91 | 177.84 | — | 123.3 126.6 | — | 213.8 | 140.1 — 162 | | — | — 176.8 | — | |

TABLE 2-continued

Genotypes of 25 ELS cultivars using 5 ELS sequence specific SSRs primers.

| SUPIMA NAME | ELS91 | | | ELS24 | | ELS29 | | | ELS30 | | | ELS35 | | |
|---|---|---|---|---|---|---|---|---|---|---|---|---|---|---|
| Barakat | 267.5 | 308.78 | 314 | 103.4 | 106.6 | 185.71 | 213.4 | 139.3 | — | 160 | — | — | — | — |
| DCH-32 | 98.96 | 118.5 | — | — | — | 185.82 | 215.1 | — | — | 161.4 | — | — | — | 184.5 |
| ELS Turkmen | 296.77 | 308.8 | 314.1 | — | 146.5 | 185.96 | 213.3 | 140.1 | — | 161.5 | — | — | — | 186.2 |
| ELS Uzbek | 297.05 | 308.68 | 314.7 | — | 126.6 | 185.61 | 213.4 | 140.5 | 152.9 | 161.9 | 138.9 | | — | 185.9 |
| ELS Spanish | 296.04 | 308.4 | 314.3 | — | 125.8 | 186.09 | 213.3 | 140.6 | — | 162 | — | — | — | 186.2 |
| ELS Yemen | — | 308.74 | 314 | — | — | — | — | 140.2 | — | 161.5 | — | — | 173.04 | 185.9 |
| ELS Chinese | — | 309.21 | 314.9 | 123.8 | 126.8 | 185.67 | 215.2 | 141.3 | 153.4 | 162.4 | — | 164.6 | — | 186.4 |
| Giza 87 | — | — | — | 123.4 | 128.3 | 186.05 | 215.2 | — | — | 161.6 | 138.8 | — | — | — |
| Pima Israeli | — | 309.04 | 314.9 | 123.7 | 126.3 | 185.82 | 213.8 | 140.7 | — | 162.2 | — | — | — | 185.8 |
| Pima Peruvian | 295.66 | — | 314.9 | — | — | — | 213.4 | 140.7 | — | 162.3 | — | 185.8 | 306.01 | 345.2 |
| Suvin Indian | — | — | — | — | — | 219.28 | 254.3 | 140.5 | — | 162.4 | 111.2 | — | — | 185.9 |

DNA extracted from mature cotton fibers was PCR amplified using the following five primer sets: ELS91, ELS24, ELS29, ELS30, and ELS35. After PCR amplification, the PCR products were analyzed by capillary electrophoresis using an ABI310 genetic analyzer. DNA fragment sizes were calculated by extrapolating size data from utilizing an internal control included with the capillary electrophoretic sample(s). Each primer set was run on PCR separately and the PCR results from capillary electrophoresis analysis of each primer set was standardized by the use of an internal standard, allowing the capillary electrophoretic chromatograms of the five different primer set PCR runs/per cultivar to be overlaid. Table 2 shows the overall PCR products produced for a specific cultivar when using the 5 primers set specified above. The numbers of each PCR product identified indicates the size/length of the PCR product in base pairs.

Table 2 demonstrates that utilizing 5 primer sets specific for variable regions of the genome for *G. barbadense* is sufficient to distinguish between the different cultivars analyzed as illustrated by 14 different genotypes.

Utilizing the methods, it is possible to profile each *G. barbadense* cultivar and develop a database with the cultivar profiles. A database comprising the *G. barbadense* can then be utilized to compare results from textile verification testing in accordance with the methods. This example demonstrates that cotton textile articles can be identified as made from a particular cultivar of the ELS species.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process step or steps, to the objective spirit and scope of the present invention. All such modifications are intended to be within the scope of the claims appended hereto.

What is claimed is:

1. A method for identifying cotton cultivar comprising:
collecting cotton fibers from a manufactured textile;
extracting genomic DNA from the cotton fibers collected, wherein the genomic DNA extracted from the mature cotton fibers comprises chloroplast DNA;
amplifying said chloroplast DNA with PCR-based techniques using one or more primer sets and thereby producing one or more amplicons;
generating a variable amplicon length polymorphism profile of said chloroplast DNA;
comparing the variable amplicon length polymorphism profile for the mature cotton fibers from the manufactured textile with a known variable amplicon length
and thereby identifying at least one cotton cultivar from the manufactured textile.

2. The method of claim 1, wherein first cotton cultivar is from the species G. barbadense.

3. The method of claim 2, wherein at least one cotton cultivar identified is from the species G. hirsutum.

4. The method of claim 1, wherein the amplifying comprises:
using at least one set of specific primers which targets length polymorphisms between a first cotton cultivar and the second cotton cultivar.

5. The method of claim 2, wherein the amplifying comprises:
using at least one set of specific primers targeting polymorphic sequences differing in length between each of at least three G. barbadense cultivars.

6. The method of claim 4, wherein the polymorphic sequence of the cotton cultivars targeted by the primers differ in another detectable physical characteristic in addition to the difference in sequence length.

7. The method of claim 6, wherein the additional detectable physical characteristic comprises a difference in a nucleotide composition.

8. The method of claim 1, wherein the genomic DNA extracted from the mature cotton fibers comprises mitochondrial DNA.

9. The method of claim 1, wherein the genomic DNA extracted from the mature cotton fibers comprises nuclear DNA.

10. The method of claim 1, wherein the analyzing of the one or more amplified products comprises detecting the size of the one or more amplified products by gel electrophoresis.

11. The method of claim 1, wherein the analyzing of the one or more amplified products comprises detecting the size of the one or more amplified products by capillary electrophoresis.

12. The method of claim 1, wherein the analyzing of the amplified chloroplast DNA comprises detecting the size of the one or more amplicons amplified by real time PCR.

13. The method of claim 4, wherein the first cotton cultivar and the second cotton cultivar are from a cotton species is selected from the group consisting of G. barbadense, G. hirsutum, G. arboreum, or G. herbaceum.

14. A method for verifying the authenticity of a manufactured textile comprising:
collecting mature cotton fibers from the manufactured textile;
extracting genomic DNA from the comprising chloroplast DNA from the mature cotton fibers collected;
amplifying said chloroplast DNA with PCR-based techniques using one or more primer sets producing one or more amplified products forming a variable amplicon length polymorphism profile for the mature cotton fibers from the textile article;
comparing the variable amplicon length polymorphism profile from the mature cotton fibers with one or more known variable amplicon length polymorphism profiles;
identifying the mature cotton fibers from the manufactured textile as belonging to one or more cotton cultivars; and
thereby determining whether the manufactures textile is authentic or counterfeit.

15. The method of claim 14, wherein at least one cotton cultivar identified is from the species G. barbadense.

16. The method of claim 14, wherein at least one of the cotton cultivars identified is from the species is G. hirsutum.

17. The method of claim 14, wherein the amplifying further comprises;

using at least one set of specific primers which targets a sequence polymorphism between the first cotton cultivar and the second cotton cultivar.

18. The method of claim 15, wherein amplifying further comprises:
using two or more sets of specific primers which targets sequence length polymorphisms between *G. barbadense* cultivars.

19. The method of claim 18, wherein the targeted sequence of the first *G. barbadense* cultivar and the second *G. barbadense* cultivar have difference in a detectable physical characteristic in addition to the sequence length polymorphisms.

20. The method of claim 19, wherein the difference in a detectable physical characteristic of the targeted sequences comprises a difference in a nucleotide composition.

21. The method of claim 14, wherein the genomic DNA extracted from the cotton fibers further comprises nuclear DNA.

22. The method of claim 14, wherein the analyzing of the amplified products comprises detecting the size of the amplified products by gel electrophoresis.

23. The method of claim 14, wherein the analyzing of the amplified products comprises detecting the size of the amplified products by capillary electrophoresis.

24. The method of claim 1, wherein the manufactured textile comprises raw cotton, ginned cotton, yarn blended with cotton and or a fabric blended with cotton.

25. The method of claim 1, wherein the amplifying if said chloroplast DNA comprises using a nested set of primers.

26. The method of claim 14, wherein the amplifying of said chloroplast DNA comprises using a nested set of primers.

27. The method of claim 26, wherein the cotton cultivar identified is from a cotton species selected from the group consisting of *G. barbadense, G hirsutum, G. arboretum*, or *G. herbaceum*.

28. The method of claim 14, wherein at least one of the cotton cultivars identified is *G. arboretum* or *G. herbaceum*.

29. The method of claim 14, wherein the one or more amplified products are produced by real-time PCR.

30. The method of claim 29, further comprising quantifying one or more of the amplified products by real-time PCR.

31. The method of claim 12, further comprising quantifying one or more of the amplified products by real-time PCR.

\* \* \* \* \*

UNITED STATES PATENT AND TRADEMARK OFFICE
CERTIFICATE OF CORRECTION

Page 1 of 2

PATENT NO. : 8,940,485 B2
APPLICATION NO. : 12/269757
DATED : January 27, 2015
INVENTOR(S) : Ming-Hwa Liang and Stephane Shu Kin So It is certified that error appears in the above-identified patent and that said Letters Patent is hereby corrected as shown below:

In the Claims:

In Column 21, line 28 (Claim 1), insert --a-- between "identifying" and "cotton cultivar"
In Column 21, line 29 (Claim 1), insert --one or more mature-- between "collecting" and "cotton fibers"
In Column 21, line 30 (Claim 1), insert --mature-- between "the" and "cotton cotton fibers collected"
In Column 21, line 33 (Claim 1), insert --a-- between "with" and "PCR-based"
In Column 21, line 34 (Claim 1), delete "techniques" and insert --technique--
In Column 21, lines 40-41 (Claim 1), insert --polymorphism profile-- between "variable amplicon length" and "and thereby identifying"

In Column 21, line 44 (Claim 2), delete "first" and insert --at least one--
In Column 21, lines 44-45 (Claim 2), insert --identified-- between "cotton cultivar" and "is from"

In Column 21, line 50 (Claim 4), delete "at least one set" and insert --two or more sets--
In Column 21, line 50 (Claim 4), delete "targets" and insert --target--
In Column 21, line 52 (Claim 4), delete "the" and insert --a-- before "second cotton cultivar"

In Column 21, line 59 (Claim 6), delete "sequence" and insert --sequences--

In Column 21, line 66 (Claim 8), insert --further-- between "mature cotton fibers" and "comprises"

In Column 22, line 28 (Claim 9), insert --further-- between "mature cotton fibers" and "comprises"

In Column 22, line 41 (Claim 13), delete "is" after "a cotton species"

In Column 22, line 48 (Claim 14), delete "from the" after "extracting genomic DNA"
In Column 22, line 50 (Claim 14), insert --a-- between "with" and "PCR-based"
In Column 22, lines 50-51 (Claim 14), delete "techniques" and insert --technique--

Signed and Sealed this
Twenty-ninth Day of December, 2015

Michelle K. Lee
*Director of the United States Patent and Trademark Office*

CERTIFICATE OF CORRECTION (continued)

U.S. Pat. No. 8,940,485 B2

In the Claims:

In Column 22, line 60 (Claim 14), delete "manufactures" and insert --manufactured--

In Column 22, line 65 (Claim 16), delete "is" between "species" and "G. hirsutum"

In Column 22, line 67 (Claim 17), delete ";" and insert --:--

In Column 23, line 4 (Claim 18), insert --the-- between "wherein" and "amplifying"
In Column 23, line 6 (Claim 18), delete "which targets" and insert --targeting--

In Column 23, line 9 (Claim 19), delete "the" between "wherein" and "targeted" and insert --a--
In Column 23, lines 9-10 (Claim 19), delete "the" between "sequence of" and "first G. barbadense" and insert --a--
In Column 23, lines 10-11 (Claim 19), delete "the" between "and" and "second G. barbadense" and insert --a--
In Column 23, line 12 (Claim 19), insert --a-- between "have" and "difference"

In Column 23, line 18 (Claim 21), insert --mature-- between "the" and "cotton fibers"

In Column 23, line 21 (Claim 22), delete "the" between "detecting" and "size" and insert --a--
In Column 23, lines 21-22 (Claim 22), insert --one or more of-- between "size of" and "the amplified products"

In Column 24, line 2 (Claim 23), delete "the" between "detecting" and "size" and insert --a--
In Column 24, line 2-3 (Claim 23), insert --one or more of-- between "size of" and "the amplified products"

In Column 23, line 7 (Claim 25), delete "if" and insert --of--

SEQUENCE LISTING

```
<160> NUMBER OF SEQ ID NOS: 10

<210> SEQ ID NO 1
<211> LENGTH: 18
<212> TYPE: DNA
<213> ORGANISM: Artificial Sequence
<220> FEATURE:
<223> OTHER INFORMATION: Sequence from a combination of Gossypium
      Barbadense and Gossypium Hirsutum

<400> SEQUENCE: 1
acttcaagga gtcagatt                                                        18

<210> SEQ ID NO 2
<211> LENGTH: 18
<212> TYPE: DNA
<213> ORGANISM: Artificial Sequence
<220> FEATURE:
<223> OTHER INFORMATION: Sequence from a combination of Gossypium
      Barbadense and Gossypium Hirsutum

<400> SEQUENCE: 2
```

```
gcaatcctca ccgagatg                                                    18
```

<210> SEQ ID NO 3
<211> LENGTH: 19
<212> TYPE: DNA
<213> ORGANISM: Artificial Sequence
<220> FEATURE:
<223> OTHER INFORMATION: Sequence from a combination of Gossypium
      Barbadense and G. Hirsutum

<400> SEQUENCE: 3

```
cctttataat cccccatca                                                   19
```

<210> SEQ ID NO 4
<211> LENGTH: 18
<212> TYPE: DNA
<213> ORGANISM: Artificial Sequence
<220> FEATURE:
<223> OTHER INFORMATION: Sequence from a combination of Gossypium
      Barbadense and Gossypium Hirsutum

<400> SEQUENCE: 4

```
gcatcagaaa aagttcaa                                                    18
```

<210> SEQ ID NO 5
<211> LENGTH: 19
<212> TYPE: DNA
<213> ORGANISM: Artificial Sequence
<220> FEATURE:
<223> OTHER INFORMATION: Sequence from a combination of Gossypium
      Barbadense and Gossypium Hirsutum

<400> SEQUENCE: 5

```
cgcaccacta tcaaatttc                                                   19
```

<210> SEQ ID NO 6
<211> LENGTH: 19
<212> TYPE: DNA
<213> ORGANISM: Artificial Sequence
<220> FEATURE:
<223> OTHER INFORMATION: Sequence from a combination of Gossypium
      Barbadense and Gossypium Hirsutum

<400> SEQUENCE: 6

```
gcttttcgac ttgagcaac                                                   19
```

<210> SEQ ID NO 7
<211> LENGTH: 19
<212> TYPE: DNA
<213> ORGANISM: Artificial Sequence
<220> FEATURE:
<223> OTHER INFORMATION: Sequence from a combination of Gossypium
      Barbadense and Gossypium Hirsutum

<400> SEQUENCE: 7

```
ccgaagacaa agaaacaca                                                   19
```

<210> SEQ ID NO 8
<211> LENGTH: 19
<212> TYPE: DNA
<213> ORGANISM: Artificial Sequence
<220> FEATURE:
<223> OTHER INFORMATION: Sequence from a combination of Gossypium
      Barbadense and Gossypium Hirsutum

<400> SEQUENCE: 8

```
cgagatcgca aaaatgaag                                              19

<210> SEQ ID NO 9
<211> LENGTH: 19
<212> TYPE: DNA
<213> ORGANISM: Artificial Sequence
<220> FEATURE:
<223> OTHER INFORMATION: Sequence from a combination of Gossypium
      Barbadense and Gossypium Hirsutum

<400> SEQUENCE: 9
ccagaaagaa gaagggaag                                              19

<210> SEQ ID NO 10
<211> LENGTH: 20
<212> TYPE: DNA
<213> ORGANISM: Artificial Sequence
<220> FEATURE:
<223> OTHER INFORMATION: Sequence from a combination of Gossypium
      Barbadense and Gossypium Hirsutum

<400> SEQUENCE: 10
cgttttggag aaaatggtca                                             20
```